United States Patent [19]

Jung

[11] Patent Number: 5,348,951
[45] Date of Patent: Sep. 20, 1994

[54] CEPHALOSPORINS

[75] Inventor: Frederic H. Jung, Rilly la Montagne, France

[73] Assignee: ICI Pharma, Cergy Cedex, France

[21] Appl. No.: 755,618

[22] Filed: Sep. 5, 1991

Related U.S. Application Data

[62] Division of Ser. No. 124,213, Nov. 23, 1987, Pat. No. 5,114,933.

[30] Foreign Application Priority Data

Nov. 21, 1986 [EP]  European Pat. Off. ........ 86402592.9

[51] Int. Cl.⁵ .................. C07D 501/24; A61K 31/545
[52] U.S. Cl. .................................. 514/202; 514/201; 540/221; 540/222
[58] Field of Search ................ 540/222, 221; 514/201, 514/202

[56]  References Cited

U.S. PATENT DOCUMENTS 5,120,728  6/1992  Nagakura ............................ 540/222

FOREIGN PATENT DOCUMENTS 0051688  3/1987  Japan .
62-209082  9/1987  Japan .

*Primary Examiner*—Nicholas S. Rizzo
*Attorney, Agent, or Firm*—Cushman, Darby & Cushman

[57]  ABSTRACT

Cephalosporin compounds having a 3-position substituent of the formula (I) are described,

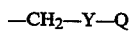

—CH₂—Y—Q                                                  (I)

wherein Y is a bond or a linking group —NR⁴—Y'—, —O—Y'—, —S—Y'— wherein R⁴ is hydrogen, various optionally substituted alkyl groups, alkenyl, alkanoyl or alkanesulphonyl, and Y' is a bond or various optionally substituted alkylene groups; and Q is a benzene ring (optionally fused to a further benzene ring so forming a naphthyl group or optionally fused to a 5 or 6 membered heterocyclic aromatic group containing 1, 2 or 3 heteroatoms selected from nitrogen, oxygen and sulphur), said benzene ring being substituted by groups R¹ and R² which are ortho with respect to one another, wherein R¹ is hydroxy or an in vivo hydrolysable ester thereof and R² is hydroxy, an in vivo hydrolysable ester thereof, carboxy, sulpho, hydroxymethyl, methanesulphonamido or ureido; or Q is a group of the formula (II) or (III):

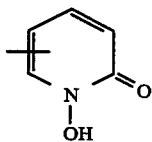

II

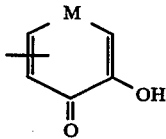

III wherein M is oxygen or a group NR³
wherein R³ is hydrogen or C₁₋₄ alkyl; ring Q being further optionally substituted.

The use of such compounds as antibacterial agents is described as are processes for their preparation and intermediates therefor.

4 Claims, No Drawings

CEPHALOSPORINS

This is a division of application No. 07/124,213, filed Nov. 23, 1987, now U.S. Pat. No. 5,114,933.

The present invention relates to cephalosporins and in particular to such compounds comprising a catechol or related group. This invention further relates to processes for their preparation, to intermediates in their preparation, to their use as therapeutic agents and to pharmaceutical compositions containing them. The compounds of this invention are antibiotics and can be used in the treatment of any disease that is conventionally treated with antibiotics for example in the treatment of bacterial infection in mammals including humans. The compounds of this invention also have non-therapeutic uses as they can be used in conventional manner in industry for example they can be used as disinfectants and food preservatives. The compounds of this invention, however, are primarily of therapeutic interest as they show a desirable profile of activity and duration in their antibacterial effect.

Investigation into new cephalosporin derivatives has been intense over the past 25 years with many thousands of patents and scientific papers having been published. A particular problem associated with the commercially available cephalosporins is the lack of potency against strains of Pseudomonas. The present invention provides cephalosporin derivatives having novel 3-position substituents, which derivatives possess good antibacterial activity and in particular against strains of Pseudomonas.

U.S. Pat. No. 4,278,793 discloses cephalosporins having a 3-position substituent of the formula: —CH$_2$Y wherein Y can be the residue of a nucleophilic compound, preferably a sulphur, nitrogen or oxygen nucleophilic compound. The emphasis therein is directed to heterocyclicthiomethyl compounds; however optionally substituted arylthiomethyl compounds are specifically mentioned. GB1496757 discloses cephalosporins having a 3-position substituent of the formulas —CH$_2$Y wherein Y can be the residue of a nucleophilic compound, this specification includes a discussion of nitrogen, carbon, oxygen and sulphur nucleophiles. Many possible values of Y are mentioned, including arylthto, aryl lower alkylthio, aryloxy and aryl lower alkoxy. GB 2148282 discloses cephalosporin compounds having a 3-position substituent of the formula: —CH$_2$R$^7$ wherein inter alia R$^7$ is optionally substituted aryl for example phenyl. The above specifications are typical of many specifications that describe cephalosporins having nucleophilic moieties linked via a methylene group to the 3-position of a cephalosporin. However, although there has been intense research over a long period of time, there has been no teaching or suggestion of the compounds of the present invention. These contain specific ring systems that are characterised by having hydroxy groups or related substituents ortho to one another. These hitherto undisclosed ring systems give rise to particularly good activity against strains of Pseudomonas. Mention should be made of Japanese Kokai 62-051688, published after the priority date of the present invention, which discloses 7-(2-(2-aminothiazol-4-yl)-2-(syn)-methoxyiminoacetamido-3-(3,4-dihydroxyphenyl)methyl-ceph-3-em-4-carboxylic acid.

Accordingly the present invention provides a cephalosporin compound having a 3-position substituent of the formula (I):

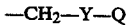

wherein Q is:
(i) a benzene ring (optionally fused to a further benzene ring so forming a naphthyl group or optionally fused to a 5 or 6 membered heterocyclic aromatic group containing 1, 2 or 3 heteroatoms selected from nitrogen, oxygen and sulphur), said benzene ring being substituted by groups R$^1$ and R$^2$ which are ortho with respect to one another, wherein R$^1$ is hydroxy or an in vivo hydrolysable ester thereof and R$^2$ is hydroxy, an in vivo hydrolysable ester thereof, carboxy, sulpho, hydroxymethyl, methanesulphonamido or ureido;

(ii) a group of the formula (II):

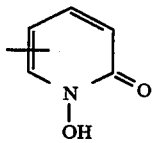

or;

(iii) a group of the formula (III):

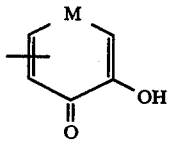

wherein M is oxygen or a group NR$^3$
wherein R$^3$ is hydrogen or C$_{1-4}$ alkyl:
ring Q (or, in the case wherein ring Q is a benzene ring and is fused to another benzene ring, either benzene ring) is optionally further substituted by C$_{1-4}$ alkyl, halo, hydroxy, hydroxy C$_{1-4}$ alkyl, cyano, trifluoromethyl, nitro, amino, C$_{1-4}$ alkylamino, di-C$_{1-4}$ alkylamino, amino C$_{1-4}$ alkyl, C$_{1-4}$ alkylamino C$_{1-4}$ alkyl, di-C$_{1-4}$ alkylamino C$_{1-4}$ alkyl, C$_{1-4}$ alkanoyl, C$_{1-4}$ alkoxy, C$_{1-4}$ alkylthio, C$_{1-4}$ alkanoyloxy, carbamoyl, C$_{1-4}$ alkylcarbamoyl, di-C$_{1-4}$ alkyl carbamoyl, carboxy, carboxy C$_{1-4}$ alkyl, sulpho, sulpho C$_{1-4}$ alkyl, C$_{1-4}$ alkanesulphonamido, C$_{1-4}$ alkoxycarbonyl, C$_{1-4}$ alkanoylamino, nitroso, thioureido, amidino, ammonium, mono-, di-or tri- C$_{1-4}$ alkylammonium or pyridinium, or a 5-membered heterocyclic ring containing 1 to 4 heteroatoms selected from oxygen, nitrogen and sulphur which is optionally substituted by 1, 2 or 3 C$_{1-4}$ alkyl or C$_{1-4}$ alkoxy groups, Y, which links into the benzene ring or the ring of formula (II) or (III), is a covalent bond or is a group —V—Y'— wherein V is oxygen, sulphur or a group —NR$^4$— and —Y'— is a covalent bond or C$_{1-4}$ alkenylene, wherein R$^4$ is hydrogen, C$_{1-4}$ alkyl optionally substituted by any of halo, hydroxy, C$_{1-4}$ alkoxy, carboxy, amino, cyano, C$_{1-4}$ alkanoylamino, phenyl or heteroaryl, or R$^4$ is C$_{2-6}$ alkenyl, C$_{1-4}$ alkanoyl or C$_{1-4}$ alkanesulphonyl.

In one aspect V is oxygen, sulphur or a group —NR⁴— and Y' is a covalent bond. In a preferred aspect Y is a covalent bond. In another preferred aspect V is oxygen, sulphur or a group —NR⁴— and Y' is a C₁₋₄alkylene group, in particular Y' is methylene.

A particularly preferred linking group Y is —NR⁴—CH₂—.

Suitable examples of R⁴ include hydrogen, methyl, ethyl, n-propyl, isopropyl, 2-fluoroethyl, 2-chloroethyl, 2-hydroxymethyl, 2-methoxyethyl, carboxymethyl, 2-aminoethyl, 2-cyanoethyl, 2-formamidoethyl, allyl, acetyl, propionyl, methanesulphonyl, furfuryl, benzyl and pyrid-4-ylmethyl. Favourably R⁴ is hydrogen, methyl, ethyl, acetyl or methanesulphonyl.

In one aspect ring Q is a benzene ring substituted by groups R¹ and R² as hereinbefore defined. R¹ is hydroxy or an in vivo hydrolysable ester thereof. In vivo hydrolysable esters are those pharmaceutically acceptable esters that hydrolyse in the human or animal body to produce the parent hydroxy compound. Such esters can be identified by administering, e.g. intravenously to a test animal, the compound under test and subsequently examining the test animal's body fluids. Suitable in vivo hydrolysable esters include C₁₋₆ alkanoyloxy for example acetoxy, propionyloxy, pivaloyloxy, C₁₋₄ alkoxycarbonyloxy for example ethoxycarbonyloxy, phenylacetoxy and phthalidyl.

Conveniently both R¹ and R² have the same value and are both hydroxy or are both in vivo hydrolysable esters, for example they are both acetoxy or both pivaloyloxy.

In one aspect Q is a ring of the formula (III). Suitably M is oxygen thus forming a pyranone ring. Suitably also M is —NH— in which case the linking group may be attached to the pyranone ring via the ring nitrogen atom or via a ring carbon atom, in the latter case allowing a greater degree of tautomerism into the hydroxypyridine tautomer. In a further aspect M is —NR³ wherein R³ is C₁₋₄ alkyl in which case the linking group Y is attached to the pyranone ring via a ring carbon atom.

In a preferred aspect Q is a benzene ring optionally fused to another benzene ring so forming a naphthyl group. As stated hereinbefore either benzene group may be substituted by R¹ and R² and by other optional substituents. Particular optional substituents are C₁₋₄ alkyl for example methyl, ethyl or isopropyl, halo for example chloro, bromo or fluoro, hydroxy, hydroxy C₁₋₄ alkyl for example hydroxymethyl, amino, nitro, C₁₋₄ alkoxy for example methoxy or ethoxy, carboxy C₁₋₄ alkyl for example carboxymethyl, C₁₋₄ alkanoylamino for example acetamido, trifluoromethyl, carboxy, carbamoyl, cyano, sulpho, C₁₋₄ alkanesulphonamido for example methanesulphonamido, C₁₋₄ alkanoyl for example acetyl, C₁₋₄ alkanoyloxy for example acetoxy or propionoxy and C₁₋₄ alkoxycarbonyl for example methoxycarbonyl. Of these, favoured substituents are sulpho, carboxymethyl, methyl, ethyl, methoxy, bromo, chloro, fluoro and nitro.

The skilled man will realise that when Q is a benzene ring up to 3 optional substituents are possible; when a naphthyl ring is formed more substituents are possible and up to 2 or 3 substituents are possible with the rings of formulae (II) and (III). In general, we prefer up to 2 optional substituents, which may be the same or different.

As stated herein above the present invention relates to cephalosporins having a novel 3-position substituent.

A particular class of cephalosporins within the present invention is that of the formula (IV),

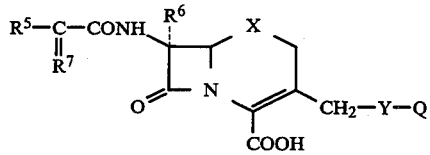

and salts and esters thereof wherein Y and Q are as hereinbefore defined;

X is sulphur, oxygen, methylene or sulphinyl;

R⁶ is hydrogen, methoxy or formamido; and R⁵ and R⁷ are groups known for such positions in the cephalosporin art.

Preferably X is sulphur.

Preferably R⁶ is hydrogen.

R⁵ is for example 2-aminothiazol-4-yl or 2-aminooxazol-4-yl each optionally substituted in the 5-position by fluorine, chlorine or bromine, or R⁵ is 5-aminoisothiazol-3-yl, 5-amino-1,2,4-thiadiazol-3-yl, 3-aminopyrazol-5-yl, 3-aminopyrazol-4-yl, 2-aminopyrimidin-5-yl, 2-aminopyrid-6-yl, 4-aminopyrimidin-2-yl, 2-amino-1,3,4-thiadiazol-5-yl or 5-amino-1-methyl-1,2,4-triazol-3-yl;

R⁷ is for example of the formula =N.O.R⁸ (having the syn configuration about the double bond) wherein R⁸ is hydrogen, (1–6C)alkyl, (3–8C)cycloalkyl, (1–3C)alkyl(3–6C)cycloalkyl, (3–6C)cycloalkyl(1–3C)alkyl, (3–6C)alkenyl, optionally substituted by carboxy, (5–8C)cycloalkenyl, (3–6C)alkynyl, (2–5C)alkylcarbamoyl, phenylcarbamoyl, benzylcarbamoyl, (1–4C)alkylcarbamoyl(1–4C)alkyl, di(1–4C)alkylcarbamoyl(1–4C)alkyl, (1–4C)haloalkylcarbamoyl(1–4C)alkyl, (1–3C)haloalkyl, (2–6C)hydroxyalkyl, (1–4C)alkoxy(2–4C)alkyl, (1–4C)alkylthio(2–4C)alkyl, (1–4C)alkanesulphinyl(1–4C)alkyl, (1–4C)alkanesulphonyl(1–4C)alkyl, (2–6C)aminoalkyl, (1–4C)alkylamino(1–6C)alkyl, (2–8C)dialkylamino(2–6C)alkyl, (1–5C)cyanoalkyl, 3-amino-3-carboxypropyl, 2-(amidinothio)ethyl, 2-(N-aminoamidinothio)ethyl, tetrahydropyran-2-yl, thietan-3-yl, 2-oxopyrrolidinyl, or 2-oxotetrahydrofuranyl, or R⁸ is of the formula V:

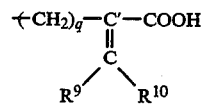

wherein q is one or two and R⁹ and R¹⁰ are independently hydrogen or C₁₋₄alkyl; or R⁸ is of the formula VI:

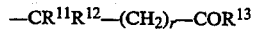

wherein r is 0–3, R¹¹ is hydrogen, (1–3C)alkyl or methylthio, R¹² is hydrogen (1–3C)alkyl, (3–7C)cycloalkyl, cyano, carboxy, (2–5C)carboxyalkyl or methanesulphonylamino, or R¹¹ and R¹² are joined to form, together with the carbon to which they are attached, a (3–7C)carbocyclic ring, and R¹³ is hydroxy, amino, (1–4C)alkoxy, (1–4C) alkylamino or of the formula NHOR¹⁴ in which R¹⁴ is hydrogen or (1–4C)alkyl or R⁷ may be of the formula =CH.R¹⁵ wherein R¹⁵ is hydrogen, halogen, (1–6C)alkyl, (3–7C)cycloalkyl, (2–6C)alkenyl, (3–7C)cycloalkenyl, phenyl or benzyl.

Particular meanings for $R^8$ are hydrogen, methyl, ethyl, isopropyl, t-butyl, cyclopropyl, cyclobutyl, cyclopentyl, cyclohexyl, methylcyclopropyl, methylcyclobutyl, methylcyclopentyl, methylcyclohexyl, cyclopropylmethyl, cyclobutylmethyl, cyclopentylmethyl, allyl, cyclopentenyl, cyclohexenyl, propargyl, methylcarbamoyl, ethylcarbamoyl, phenylcarbamoyl, benzylcarbamoyl, 2-chloroethyl, 2-fluoroethyl, 2-bromoethyl, 2-hydroxyethyl, 3-hydroxypropyl, 2-methoxyethyl, 2-ethoxyethyl, 2-methylthio-ethyl, 2-methanesulphinylethyl, 2-methanesulphonyl-ethyl, 2-aminoethyl, 3-aminopropyl, 2-methylamino ethyl, 2-dimethylaminoethyl, cyanomethyl, 2-cyanoethyl, azidomethyl, 2-azidoethyl, ureidomethyl, 3-amino-3-carboxypropyl, 2-(amidino)ethyl, 2-(N-aminoamidino)-ethyl, tetrahydropyran-2-yl, thietan-3-yl, 2-oxopyrrolidinyl and 2-oxotetrahydrofuran-3-yl, or, when $R^8$ is of the formula V in which q is 1 or 2, a particular meaning for $R^8$ is when $R^9$ and $R^{10}$ are hydrogen or methyl, or, when $R^8$ is of the formula VI, a particular meaning for $R^8$ is when r=0 and $R^{11}$ is hydrogen, methyl or methylthio, $R^{12}$ is hydrogen, methyl, cyclopropyl, cyclobutyl, cyclopentyl, cyclohexyl, cyano, carboxy, carboxymethyl, 2-carboxyethyl or methanesulphonylamino, or when $R^{11}$ and $R^{12}$ are joined to form, together with the carbon to which they are attached, a cyclopropane, cyclobutane, cyclopentane, cyclohexane or cycloheptane ring and $R^{13}$ is hydroxy, amino, methoxy, ethoxy, methylamino, ethylamino, or of the formula $NHOR^{14}$ in which $R^{14}$ is hydrogen, methyl or ethyl.

Preferably $R^8$ is $C_{1-6}$ alkyl for example methyl or ethyl, 1-carboxycyclobutyl, 1-carboxycyclopentyl, or 2-carboxyprop-2-yl. In particular $R^8$ is 2-carboxyprop-2-yl.

Particular meanings for $R^{15}$ are hydrogen, methyl, ethyl or chlorine.

Preferred compounds of the present invention include:

3-(3,4-dihydroxybenzoylaminomethyl)-7-[2-(2-aminothiazol-4-yl)-2-((Z)-1-carboxy-1-methylethoxyimino)acetamido]ceph-3-em-4-carboxylic acid; and 3-(3,4-dihydroxybenzyl)-7-[2-(2-aminothiazol-4-yl)-2-((Z)-1-carboxy-1-methylethoxyimino)acetamido]-ceph-3-em-4-carboxylic acid.

The cephalosporin derivatives referred to herein are generally named in accordance with the 'cephem' nomenclature and numbering system proposed in J.A.C.S. 1962, 84, 3400.

It will be realised, of course, that the present invention covers all isomeric and tautomerlc forms of the aforementioned compounds. For example the rings of the formula (III) may be in pyranone or hydroxypyridine form.

As stated hereinbefore the compounds of this invention ar primarily intended for use in therapy. Therefore in a preferred aspect the present invention provides a cephalosporin compound having a 3-position substituent of the formula I or a pharmaceutically acceptable salt or ester thereof. Suitable salts include acid addition salts such as hydrochloride, hydrobromide, citrate, maleate and salts formed with phosphoric and sulphuric acid. In another aspect suitable salts are base salts such as an alkali metal salt for example sodium or potassium, an alkaline earth metal salt for example calcium or magnesium, an organic amine salt for example triethylamine, morpholine, N-methylpiperidine, N-ethylpiperidine, procaine, dibenzylamine, or N,N-dibenzylethylamine.

In order to use a compound of the present invention or a pharmaceutically acceptable salt or ester thereof for the therapeutic treatment of mammals including humans, in particular in treating infection, it is normally formulated in accordance with standard pharmaceutical practice as a pharmaceutical composition.

Therefore in another aspect the present invention provides a pharmaceutical composition which comprises a cephalosporin compound having a 3-position substituent of the formula I or a pharmaceutically acceptable salt or ester thereof and a pharmaceutically acceptable carrier.

The pharmaceutical compositions of this invention may be administered in standard manner for the disease condition that is desired to treat, for example by oral, rectal or parenteral administration. For these purposes it may be formulated by means known to the art into the form of, for example, tablets, capsules, aqueous or oily solutions or suspensions, emulsions, dispersible powders, suppositories and sterile injectable aqueous or oily solutions or suspensions.

In addition to the pharmaceutically acceptable cephalosporin derivative of the present invention the pharmaceutical composition of the invention may also contain, or be co-administered with, one or more known drugs selected from other clinically useful antibacterial agents (for example other beta-lactams or aminoglycosides), inhibitors of beta-lactamase (for example clavulanic acid), renal tubular blocking agents (e.g. probenicid) and inhibitors of metabolising enzymes (for example inhibitors of peptidases, for example Z-2-acylamino-3-substituted propenoates).

A preferred pharmaceutical composition of the invention is one suitable for intravenous, subcutaneous or intramuscular injection, for example a sterile injectable containing between 1 and 50% w/w of the cephalosporin derivative, or one suitable for oral administration in unit dosage form, for example a tablet or capsule which contains between 100 mg. and 1 g. of the cephalosporin derivative.

The pharmaceutical compositions of the invention will normally be administered to man in order to combat infections caused by bacteria, in the same general manner as that employed for cephalothin, cefoxitin, cephradine, ceftazidime and other known clinically used cephalosporin derivatives, due allowance being made in terms of dose levels for the potency of the cephalosporin derivative of the present invention relative to the known clinically used cephalosporins. Thus each patient will receive a daily intravenous, subcutaneous or intramuscular dose of 0.05 to 30 g., and preferably 0.1 to 10 g., of the cephalosporin derivative, the composition being administered 1 to 4 times per day, preferably 1 or 2 times a day. The intravenous, subcutaneous and intramuscular dose may be given by means of a bolus injection. Alternatively the intravenous dose may be given by continuous infusion over a period of time. Alternatively each patient will receive a daily oral dose which is approximately equivalent to the daily parenteral dose. Thus a preferred daily oral dose is 0.5 to 10 g. of the cephalosporin derivative, the composition being administered 1 to 4 times per day.

In a further aspect the present invention provides a process for preparing a cephalosporin compound having a 3-position substituent of the formula I, which process comprises;
(a) reacting a cephalosporin compound having a 3-position substituent of the formula: —$CH_2L$ wherein L is a leaving group, with a source of —Y—Q wherein Y and Q are as hereinbefore defined;
(b) for preparing a compound wherein Y is a group —V—Y'—, reacting a cephalosporin compound having a 3-position substituent of the formula: —$CH_2VH$ with a source of —Y'—Q wherein V, Y' and Q are as hereinbefore defined;
(c) for preparing compounds of the formula (IV), reacting a compound of the formula (VII) with a compound of the formula (VIII) or a reactive derivative thereof:

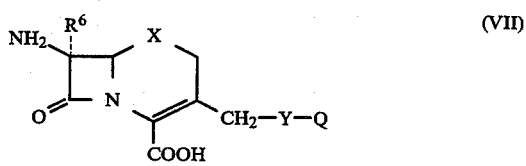

wherein $R^5$, $R^6$, $R^7$, X, Y and Q are as hereinbefore defined or d) for compounds of the formula (IV) wherein $R^7$ is a group =$NOR^8$, reacting a compound of the formula (IX):

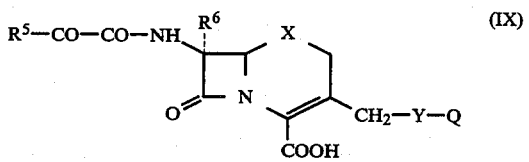

wherein $R^5$, $R^6$, X, Y and Q are as hereinbefore defined, with a compound of the formula, $R^8ONH_2$ wherein $R^8$ is as hereinbefore defined; or e) for compounds of the formula (IV) wherein $R^7$ is a group =$NOR^8$ and $R^8$ is other than hydrogen, reacting a compound of the formula (IV) as hereinbefore defined wherein $R^7$ is a group =NOH with a compound of the formula (X):

wherein $L^1$ is a leaving group and $R^{16}$ is a group $R^8$ other than hydrogen: or f) for compounds of the formula (IV) forming a group $R^5$ by cyclising an appropriate precursor thereof: wherein any functional groups are optionally protected:

and thereafter, if necessary:
i) removing any protecting group,
ii) for preparing in vivo hydrolysable esters, esterifying corresponding hydroxy groups,
iii) converting compounds wherein X is S to compounds wherein X is sulphinyl and vice versa,
iv) converting compounds wherein $R^4$ is one value to compounds wherein $R^4$ has another value,
v) forming a pharmaceutically acceptable salt.

In the reaction between a cephalosporin compound having a 3-position substituent of the formula: —$CH_2L$ and a source of —Y—Q, conveniently L is a leaving group such as halo for example iodo, bromo or chloro, or is $C_{1-4}$ alkanoyloxy for example acetoxy. This reaction is most suitable for forming cephalosporin compounds wherein the 3-position substituent is substituted benzyl or substituted naphthylmethyl. Typically the reaction is performed in the presence of boron trifluoride catalyst in a substantially inert solvent such as acetonitrile at a non-extreme temperature for example ambient.

The reaction between a cephalosporin compound having a 3-position substituent of the formula: —$CH_2VH$ and a source of —Y'—Q, may be performed in conventional manner. For example reference may be made to GB 1496757. In a preferred aspect cephalosporin compounds having a 3-position substituent of the formula: —$CH_2N(R^4)$—$CH_2$—Q can be prepared by reacting a cephalosporin having a 3-$CH_2NHR_4$ substituent with an aldehyde (or equivalent) of the formula: QCHO in the presence of a reducing agent for example a borohydride. Such reductive aminations can be performed in conventional manner in a substantially inert solvent for example methanol at a non-extreme temperature for example ambient.

The cephalosporin starting materials for these reactions are known from the art, or are made by methods analogous thereto. See for example GB 1496757, EP-A-127992 and EP-A-164944.

The reaction between compounds of the formulae (VII) and (VIII) is performed under conditions conventional in the cephalosporin art, for example under standard acylation conditions wherein for example the acid is activated as an acid bromide, acid chloride, anhydride or activated ester, or the reaction is performed in the presence of a coupling reagent such as dicyclohexylcarbodi-imide.

The compounds of the formula (VII) can be prepared in a manner analogous to that described for the compounds of the formula (I), with the 7-amino group being optionally protected.

The reaction between compounds of the formula (IX) and $R^8ONH_2$ is performed under conditions standard in the general chemical and/or cephalosporin art. The compounds of the formula (IX) can be prepared in a manner analogous to that described for the compounds of the formula (I).

The reaction between the compound of the formula (IV) wherein $R^7$ is a group =NOH and a compound of the formula (X) is performed under conditions standard in the general chemical and/or cephalosporin art.

A group $R^5$ may be formed by cyclizing an appropriate precursor. For example compounds of the formulae (XI) and (XII):

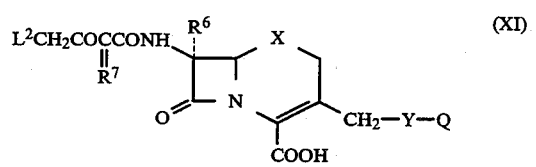

wherein $R^7$, $R^6$, X, Y and Q are as hereinbefore defined and $L^2$ is a leaving group, may be reacted to form a 2-aminothiazol-4-yl group. A nitrogen atom of the thiourea may be optionally protected during this cyclization.

The compounds of the formula (XI) can be prepared in a manner analogous to that described for the compounds of the formula I.

The compounds of the formulae (VIII), (X) and $R^8ONH_2$ are known from, or can be made by the methods of, the general chemical and/or cephalosporin art.

The compounds of the formulae (VII), (IX) and (XI) are novel and as such form a further aspect of the present invention.

In the process of this invention any functional group can be optionally protected, if appropriate. Such protecting groups may in general be chosen from any of the groups described in the literature or known to the skilled chemist as appropriate for the protection of the group in question, and may be introduced by conventional methods.

Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

Specific examples of protecting groups are given below for the sake of convenience, in which "lower" signifies that the group to which it is applied preferably has 1-4 carbon atoms. It will be understood that these examples are not exhaustive. Where specific examples of methods for the removal of protecting groups are given below these are similarly not exhaustive. The use of protecting groups and methods of deprotection not specifically mentioned Is of course within the scope of the invention.

A carboxyl protecting group may be the residue of an ester-forming aliphatic or araliphatic alcohol or of an ester-forming phenol, silanol or stannanol (the said alcohol, phenol, silanol or stannanol preferably containing 1-20 carbon atoms).

Examples of carboxyl protecting groups include straight or branched chain (1-12C)alkyl groups (e.g. isopropyl, t-butyl); halo lower alkyl groups (e.g. 2-iodoethyl, 2,2,2-trichloroethyl); lower alkoxy lower alkyl groups (e.g. methoxymethyl, ethoxymethyl, isobutoxymethyl); lower aliphatic acyloxy lower alkyl groups, (e.g. acetoxymethyl, propionyloxymethyl, butyryloxymethyl, pivaloyloxymethyl); lower alkoxycarbonyloxy lower alkyl groups (e.g. 1-methoxycarbonyloxyethyl, 1-ethoxycarbonyloxyethyl); aryl lower alkyl groups (e.g. p-methoxybenzyl, o-nitrobenzyl, p-nitrobenzyl, benzhydryl and phthalidyl) tri(lower alkyl)silyl groups (e.g. trimethylsilyl and t-butyldimethylsilyl); tri(lower alkyl)silyl lower alkyl groups (e.g. trimethylsilylethyl) and (2-6C)alkenyl groups (e.g. allyl and vinylethyl).

Methods particularly appropriate for the removal of carboxyl protecting groups include for example acid-, base-, metal- or enzymically-catalysed hydrolysis.

Examples of hydroxyl protecting groups include lower alkanoyl groups (e.g. acetyl); lower alkoxycarbonyl groups (e.g. t-butoxycarbonyl) halo lower alkoxycarbonyl groups (e.g. 2-iodoethoxycarbonyl, 2,2,2-trichloroethoxycarbonyl); aryl lower alkoxycarbonyl groups (e.g. benzoyloxycarbonyl, p-methoxybenzyloxycarbonyl, o-nitrobenzyloxycarbonyl, p-nitrobenzyloxycarbonyl); tri lower alkylsilyl (e.g. trimethylsilyl, t-butyldimethylsilyl) and aryl lower alkyl (e.g. benzyl) groups. In addition two hydroxy groups substituted on adjacent carbon atoms, for example in the catechol moiety, may be protected in the form of a cyclic acetal such as the methylenedioxy moiety.

Examples of amino protecting groups include formyl, aralkyl groups (e.g. benzyl and substituted benzyl, e.g. p-methoxybenzyl, nitrobenzyl and 2,4-dimethoxybenzyl, and triphenylmethyl) di-p-anisylmethyl and furylmethyl groups; acyl (e.g. alkoxycarbonyl and aralkoxycarbonyl e.g. t-butoxycarbonyl and benzyloxycarbonyl), trialkylsilyl (e.g. trimethylsilyl and t-butyldimethylsilyl), alkylidene (e.g. methylidene), benzylidene and substituted benzylidene groups, and the phthalimido group.

Esterification of hydroxy groups (i.e. $R^1$ and $R^2$) to form in vivo hydrolysable esters is performed in conventional manner. Reduction of a cephalosporin sulphoxide to a cephalosporin and oxidation of a sulphoxide to a sulphide are performed according to methods known in the art. An example of converting one group $R^4$ to another group $R^4$ is the acylation of —NH— to —N(COC$_{1-4}$alkyl)— or to —N(SO$_2$C$_{1-4}$alkyl)—.

The following biological test methods, data and Examples serve to illustrate this invention.

Antibacterial Activity

The pharmaceutically acceptable cephalosporin compounds of the present invention are useful antibacterial agents having a broad spectrum of activity in vitro against standard laboratory microorganisms, both Gram-negative and Gram-positive, which are used to screen for activity against pathogenic bacteria. The antibacterial spectrum and potency of a particular compound may be determined in a standard test system. The compounds have particularly high activity in vitro against strains of *Pseudomonas aeruginosa*.

The antibacterial properties of the compounds of the invention may also be demonstrated in vivo in conventional mouse protection tests.

In addition representative compounds of this invention show prolonged duration, as evidenced by half-life values, in test animals.

Cephalosporin derivatives have generally been found to be relatively non-toxic to warm-blooded animals, and this generalisation holds true for the compounds of the present invention. Compounds representative of the present invention were administered to mice at doses in excess of those required to afford protection against bacterial infections, and no overt toxic symptoms or side effects attributable to the administered compounds were noted.

The following results were obtained for representative compounds on a standard in vitro test system using Isosensitest agar medium. The antibacterial activity is described in terms of the minimum inhibitory concentration (M1C) determined by the agar-dilution technique with an inoculum size of $10^4$ CFU/spot.

| ORGANISM | MIC (μl/ml) EXAMPLE | | | |
|---|---|---|---|---|
| | 3 | 6 | 9 | 20 |
| P. aeruginosa PU21 (A8101028) | 4 | 0.25 | 0.25 | 2 |
| Ent. cloacae P99 (A8401054) | 4 | 2 | 4 | 8 |
| Serr. marcesens (A8421003) | 0.5 | 0.25 | NA | 4 |
| Pr. morganii (A8433001) | 2 | 0.25 | 1 | 16 |

-continued

| ORGANISM | MIC (μl/ml) EXAMPLE | | | |
|---|---|---|---|---|
| | 3 | 6 | 9 | 20 |
| Kleb. aerogenes (A8391027) | 0.125 | 0.06 | 0.06 | 4 |
| E. coli DCO (A8341098) | 0.125 | 0.06 | 0.125 | 1 |
| St. aureus 147N (A8601052) | 4 | 16 | 16 | 8 |
| S. dublin (A8369001) | 2 | 0.25 | 0.25 | 8 |
| Strep. pyogenes (A681018) | 0.008 | 0.125 | 0.25 | NA |

In the following Examples the following abbreviations are used:
AcOH=acetic acid
DMF=dimethylformamide
DMSO=dimethylsulphoxide
EtOAc=ethyl acetate
EtOH=ethanol
HPLC=high performance liquid chromatography
MeOH=methanol
NMR=nuclear magnetic resonance spectroscopy
TEA=triethylamine
TFA=trifluoroacetic acid The NMR spectra are taken at 90 MHz and are quoted in terms of delta values in parts per million (ppm) with reference to tetramethylsilane (delta=0). The solvent used was DMSOd$_6$/CD$_3$COOD/TFA except where otherwise indicated. In the quotation of NMR data s=singlet, d=doublet, t=triplet, q=quartet, m=multiplet, br=broad.

EXAMPLES 1-7

The following general procedure was used for the preparation of the compounds of Examples 1-7, of which particulars are given in Tables I and II.

To a suspension of the appropriate 7-substituted-3-aminomethyl-ceph-3-em-4-carboxylic acid (0.5 mmole) in MeOH (15 ml) containing a few drops of water, and maintained at pH 5.5-6.0 was added 3,4-dihydroxybenzaldehyde (0.55 mmole) and then sodium cyanoborohydride (0.5 mmole).

The pH was maintained at pH 5.5-6.0 by addition of sodium bicarbonate or acetic acid as appropriate, and further portions of sodium cyanoborohydride were added over 4 hours until none of the cephalosporin starting material remained (monitored by HPLC). The solvents were evaporated and the mixture purified on a Diaion HP20SS resin column using MeOH/H$_2$O mixtures of increasing proportions of MeOH and containing AcOH (1%). Evaporation and freeze drying of the appropriate fractions gave the product in the yield indicated.

Particulars of the compounds prepared, and the yields obtained, are given in Table I. NMR characterising data is given in Table II.

TABLE I

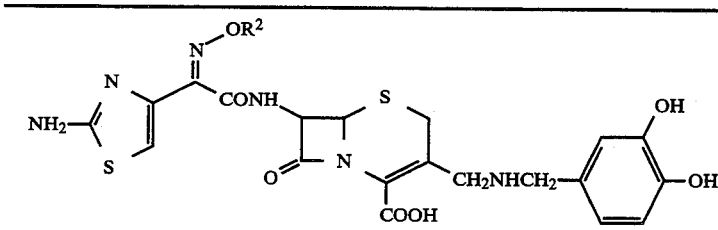

| Example No. | R2 | Yield (%) | Footnotes |
|---|---|---|---|
| 1 | —C$_2$H$_5$ | 27 | |
| 2 | —CH$_2$CH$_2$F | 40 | |
| 3 | —CH$_2$CH$_2$Cl | 57 | |
| 4 | —CH$_3$ | 25 | |
| 5 | —CH$_2$CF$_3$ | 33 | |
| 6 | —C(CH$_3$)$_2$—COOH | 13 | |
| 7 | —CH$_2$—COOH | 48 | 1 |

Footnotes
1. The general method indicated was used to prepare the diacetoxy derivative using 3,4-diacetoxybenzaldehyde instead of the 3,4-dihydroxy compound and the resulting compound 7-[2-(2-aminothiazol-4-yl)-2-((Z)-carboxymethoxyimino)acetamido]-3-(3,4-diacetoxybenzyl)aminomethylceph-3-em-4-carboxylic acid (130 mg) deprotected by dissolving in H$_2$O (50 ml) containing ammonium carbonate (100 mg) at pH 7-7.5. The solution was left to stand for 2 days until no cephalosporin starting material remained. The mixture was purified on a Diaion HP20SS resin column and isolated as described above.

TABLE II

NMR data for the compounds of Table I taken at 90 MHz in DMSOd$_6$/CD$_3$CO$_2$D/TFAd

| Example No. | Delta Values (ppm). |
|---|---|
| 1 | 2.5(t,3H); 3.65(m, 2H); 3.8(m, 2H); 4.0(m, 2H); 4.25(q, 2H); 5.15(d, 1H); 5.85(d, 1H); 6.75(s, 2H); 6.90(s, 1H); 7.0(s, 1H). |
| 2 | 3.65(m, 2H); 385(m, 2H); 4.0(m, 2H); 4.4(m, 2H); 4.6(t, 1H); 5.0(t, 1H); 5.2(d, 1H); 5.85(d, 1H); 6.75(s, 2H); 6.9(s, 1H); 7.0(s, 1H). |
| 3 | 3.65(m, 2H); 3.7–4.1(m, 6H); 4.4(t, 2H); 5.15(d, 1H); 5.85(d, 1H); 6.75(s, 2H); 6.9(s, 1H); 7.05(s, 1H). |
| 4 | 3.65(m, 2H); 3.85(m, 2H); 4.0(m, 2H); 4.0(s, 3H); 5.15(d, 1H); 5.85(d, 1H); 6.75(s, 2H); 6.9(s, 1H); 7.0(s, 1H). |
| 5 | 3.65(m, 2H); 3.85(m, 2H); 4.0(m, 2H); 4.75(q, 2H); 5.2(d, 1H); 5.85(d, 1H); 6.8(s, 2H); 6.9(s, 1H); 7.05(s, 1H). |
| 6 | 1.55(s, 6H); 3.65(m, 2H); 3.7–3.9(m, 2H); 4.0(m, 2H); 5.15(d, 1H); 5.9(d, 1H); 6.75(s, 2H); 6.9(s, 1H); 7.05(s, 1H). |
| 7 | 3.6–4.1(m, 6H); 4.75(s, 2H); 5.2(d, 1H); 5.9(d, 1H); |

TABLE II-continued

NMR data for the compounds of Table I taken at 90 MHz in DMSOd$_6$/CD$_3$CO$_2$D/TFAd

| Example No. | Delta Values (ppm). |
|---|---|
| | 6.8(s, 2H); 6.85(s, 1H); 7.05(s, 1H). |

EXAMPLE 8

3-(3,4-Dihydroxybenzylaminomethyl)-7-[2-(aminothiazol-4-yl)-2-((Z)-1-carboxycyclopentyloxyimino)acetamido]-ceph-3-em-4-carboxylic acid To a suspension of 3-aminomethyl-7-[2-(aminothiazol-4-yl)-2-((Z)-1-carboxycyclopentyloxyimino)acetamido]ceph-3-em-4-carboxylic acid (153 mg) in water (10 ml) with sufficient triethylamine to obtain a solution (pH 7.5) was added 3,4-dihydroxybenzaldehyde (41 mg) and then sodium cyanoborohydride (19 mg). The pH was adjusted and further maintained at pH 5.4 and further portions (×4) of sodium cyanoborohydride and 3,4-dihydroxybenzaldehyde added over 24 hours until no cephalosporin starting material remained. The aqueous solution was washed three times with ether and concentrated, and the crude mixture purified by HPLC on an octadecylsilane column using MeOH/water/AcOH, 20-30:79-69:1 as eluant. Evaporation and freeze drying yielded 80 mg (48%) of the title compound, NMR in DMSOd$_6$+CD$_3$CO$_2$D+TFA$_d$; 1.81(s,4H); 2.15(m,4H); 3.4 to 4.2(m,6H); 5.17(d,1H); 5.9(d,1H); 6.76(br.s,2H); 6.89(br.s,1H); 7.04(s,1H).

EXAMPLES 9-20

The following general procedure was used for the preparation of the compounds of Examples 9-20, of which particulars are given in Tables III and IV.

To a solution of 7-amino-3-acetoxymethylceph-3-em-4-carboxylic acid (7-ACA) (1 mmole) in acetonitrile/BF$_3$.Et$_2$O (4/1) at room temperature, was added the appropriate dihydroxy benzene or naphthalene derivative (1 mmole). Stirring was continued at room temperature for 2 to 3 hours, the progress of the reaction being followed by analytical HPLC. At the end of the reaction the solvents were evaporated and the crude product purified by medium pressure chromatography on a Diaion HP20SS column, using MeOH/water with 1% AcOH, the percentage of MeOH being slowly increased from 0 to 100%.

The 7-amino cephalosporin intermediate thus produced was dissolved in CH$_2$Cl$_2$ with 4-5 equivalents of bis-trimethylsilylacetamide (BSA) at room temperature under argon, several hours being necessary to achieve complete dissolution. To this solution was added a solution of the appropriate 7-side chain carboxylic acid (carboxy groups on the oxime protected as the t-butoxy derivative and the aminothiazolyl protected as the trityl derivative) in the form of the acid chloride or an active ester (e.g. with N-hydroxybenzotriazole (HOBT)). The mixture was shaken at room temperature for several hours, the solvent evaporated and the product treated with TFA/water at room temperature for two hours to remove all protecting groups. The compound was then purified by HPLC or medium pressure chromatography.

Particulars of the compounds prepared, and the yields obtained, are given in Table III. NMR characterising data is given in Table IV.

TABLE III

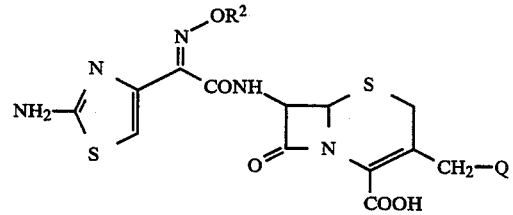

| Example No. | R2 | Q | Yield (%) |
|---|---|---|---|
| 9 | CH$_3$—C(COOH)—CH$_3$ | 2,3-dihydroxyphenyl | 22 |
| 10 | CH$_3$ | 2,3-dihydroxyphenyl | 30 |
| 11 | CH$_3$—C(COOH)—CH$_3$ | 2,3-dihydroxynaphthyl | 17 |
| 12 | CH$_3$ | 2,3-dihydroxynaphthyl | 20 |
| 13 | CH$_3$—C(COOH)—CH$_3$ | 2,3-dihydroxy-6-sulfonaphthyl | 62 |
| 14 | CH$_3$—C(COOH)—CH$_3$ | 1,2-dihydroxynaphthyl | 10 |
| 15 | —C$_2$H$_5$ | 3,4-dihydroxy-CH$_2$COOH phenyl | 37 |

TABLE III-continued

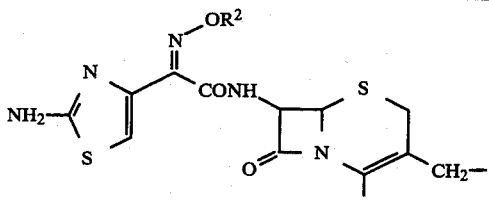

| Example No. | R2 | Q | Yield (%) |
|---|---|---|---|
| 16 | —C$_2$H$_5$ | 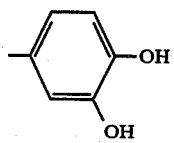 | 24 |
| 17 | —C$_2$H$_5$ | 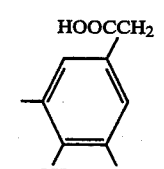 | 20 |
| 18 | —C$_2$H$_5$ | 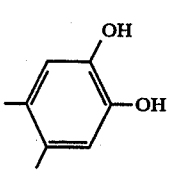 | 21 |
| 19 | —C$_2$H$_5$ | 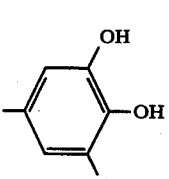 | 12 |
| 20 | —C$_2$H$_5$ | 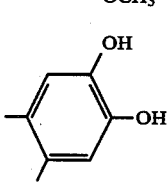 | 42 |

TABLE IV

NMR data for the compounds of Table III taken at 90 MHz in DMSOd$_6$/AcOD/TFA.

| Example No. | Delta values (ppm) |
|---|---|
| 9 | 1.52(s, 6H); 3.35 and 3.5(2d, 2H); 3.2–4.1(m, 2H); 5.17(d, 1H), 5.77(d, 1H); 6.5–6.9(m, 3H); 7.05(s, 1H). |
| 10 | 3.2 and 3.5(2d, 2H); 3.3–4.1(m, 2H); 4.0(s, 3H); 5.17(d, 1H); 5.7(d, 1H); 6.5–6.85(m, 3H); 7.0(s, 1H). |
| 11 | 1.5(s, 6H); 3.14(m, 2H); 4.4(m, 2H); 5.14(d, 1H); 5.7(d, 1H); 7.05(s, 1H); 7.05–8(m, 5H). |
| 12 | 3.1(m, 2H); 4(s, 3H); 4.4(m, 2H); 5.1(d, 1H); 5.6(d, 1H); 7(s, 1H); 7.1(s, 1H); 7.1–8(m, 4H). |
| 13 | 1.5(s, 6H); 3.1(m, 2H); 4.4(m, 2H); 5.1(d, 1H); 5.7(d, 1H); 7.05(s, 1H): 7.15(s, 1H); 7.6(m, 2H); 8.2(s, 1H). |
| 14 | 1.5(s, 6H); 3.1 and 3.4(2d, 2H); 4.1–4.3(m, 2H); 5.15(d, 1H); 5.75d, 1H); 7.08(m, 2H); 7.2–8.3(m, 4H). |
| 15 | 1.27(t, 3H); 3.1 and 3.4(2d, 2H); 3.44(m, 2H); 3.5–3.8(m, 2H); 4.24(q, 2H); 5.15(d, 1H); 5.75(d, 1H); |

TABLE IV-continued

NMR data for the compounds of Table III taken at 90 MHz in DMSOd$_6$/AcOD/TFA.

| Example No. | Delta values (ppm) |
|---|---|
|  | 6.6(s, 2H); 7.0(s, 1H). |
| 16 | 1.25(t, 3H); 3.15 and 3.45(2d, 2H); 3.2–4(m, 2H); 4.2(q, 2R), 5.15(d, 1H); 5.7(d, 1H); 6.4–6.8(m, 2H) 6.7(s, 1H); 7.0(s, 1H). |
| 17 | 1.15(t, 3H); 3.1–3.3(m, 2H); 3.75(m, 2H); 4.2(q, 2H); 5.15(d, 1H); 5.65(d, 1H); 6.5(s, 1H); 6.6(s, 1H); 6.95(s, 1H). |
| 18 | 1.15(t, 3H); 2.05(s, 3H); 3.1 and 3.35(2d, 2H); 3.5 and 3.75(2d, 2H); 4.24(q, 2H); 5.15(d, 1H); 5.7(d, 1H); 6.55(2s, 2H); 7.0(s, 1H). |
| 19 | 1.25(t, 3H); 3.7(s, 3H); 3–4(m, 4H); 4.24(q, 2H); 5.1(d, 1H); 5.65(d, 1H); 6.45(s, 2H); 6.95(s, 1H). |
| 20* | 1.05(t, 3H); 1.26(t, 3H); 2.45(q, 2H); 3.1 and 3.4(2d, 2H); 3.5 and 3.8(2d, 2H); 4.24(q, 2H); 5.15(d, 1H); 5.7(d, 1H); 6.55(s, 2H); 7.0(s, 1H). |

*Solvent = CF$_3$CO$_2$D/CD$_3$CO$_2$D/DMSOd$_6$

EXAMPLE 21

7-[2-(2-Aminothiazol-4-yl)-2-((Z)-ethoxyimino)acetamido-3-(N-3,4-diacetoxybenzyl )aminomethyl]-ceph-3-em-4-carboxylic acid (190 mg, 0.3 mmol) was suspended in acetonitrile (4 ml), the suspension was cooled to 0° C., and treated, in quick succession, with triethylamine (61 mg; 83 μl, 0.6 mmol) and acetyl chloride (24 mg, 22 μl, 0.3 mmol). The mixture was stirred at 0° for 1 hour, the acetonitrile removed under reduced pressure and the residue so obtained applied to a Diaion HP 20 SS resin column in H$_2$O/DMF. The column was developed by gradient elution (H$_2$O—20% CH$_3$CN/H$_2$O), the appropriate fractions combined, acetonitrile removed and 7-[2-(2-aminothiazol-4-yl)-2((Z)-ethoxyimino)acetamido-3-(N-acetyl-N-3,4-diacetoxybenzyl)aminomethyl]-ceph-3-em-4-carboxylic acid obtained (in 36% yield) by freeze-drying; NMR (d$_6$DMSO,d$_4$HOAC) 1.18(t,3H); 2.02, 2.12(s,s,3H, 2 rotamers); 2.21(s, 6H); 3.30(d, 1H); 3.45(d,d, 1H); 4.09(q, 2H); 4.2–4.65(m, 2H); 5.03, 5.06(d,d, 1H, 2 rotamers); 5.76(d,d, 1H, 2 rotamers), 6.61(s, 1H), 7–7.25(m, 3H).

EXAMPLE 22

7-[2-(2-Aminothiazol-4-yl)-2-((Z)-ethoxyimino)acetamido-3-(N-3,4-diacetoxybenzyl)aminomethyl]-ceph-3-em-4-carboxylic acid (250 mg, 0.4 mmol) was suspended in acetonitrile (5 ml), the suspension cooled to 0° C., treated with triethylamine (80 mg, 109 μl, 0.8 mmol) and, subsequently, with methanesulphonylchlorlde (45 mg, 31 μl, 0.4 mmol). The mixture was stirred for 10 minutes before adding further triethylamine (80 mg, 0.8 mmol). After stirring for a further 1½ hours the mixture was poured on to H$_2$O (75 ml) and the solution purified by chromatography on Diaion HP 20 SS resin (gradient elution, H$_2$O—20% CH$_3$CN/H$_2$O. Appropriate fractions were combined, acetonitrile removed under reduced pressure and triethylammonium 7-[2-(2-aminothiazol-4-yl )-2-((Z)-ethoxyimino)acetamido-3-(N-3,4-diacetoxybenzyl-N-methanesulphonyl)aminomethyl]-ceph-3-em-4-carboxylate isolated by freeze-drying (48% yield); NMR (d$_6$DMSO,d$_4$HOAc) 1.16(t, 9H); 1.2(t, 3H); 2.2(s, 3H); 2.22(s, 3H); 2.97(s, 3H); 3.08(q, 6H); 3.24(s, 2H); 4.08(q, 2H); 4.19(d, 1H); 4.20(br, 2H); 4.45(d, 1H); 4.77(d, 1H); 5.68(d, 1H); 6.7(s, 1H); 7.1–7.3(m, 3H).

I claim:

1. A cephalosporin compound of the formula (IV):

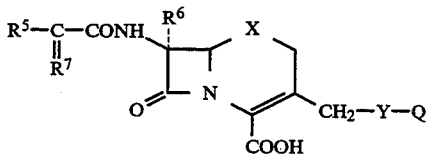

or a salt or ester thereof; wherein,
X is sulphur or sulphinyl;
$R^6$ is hydrogen, methoxy or formamido;
$R^5$ is 2-aminothiazol-4-yl or 2-aminooxazol-4-yl each unsubstituted or substituted in the 5-position by fluorine, chlorine or bromine, or $R^5$ is 5-aminoisothiazol-3-yl, 5-amino-1,2,4-thiadiazol-3-yl, 3-aminopyrazol-5-yl, 3-aminopyrazol-4-yl, 2-aminopyrimidin-5-yl, 2-aminopyrid-6-yl, 4-aminopyrimidin-2-yl, 2-amino-1,3,4-thiadiazol-5-yl or 5-amino-1-methyl-1,2,4-triazol-3-yl;
$R^7$ is of the formula $=N.O.R^8$ (having the syn configuration about the double bond) wherein $R^8$ is hydrogen, (1–6C)alkyl, (3–8C)cycloalkyl, (1–3C)alkyl(3–6C)cycloalkyl, (3–6C)cycloalkyl(1–3C)alkyl, (3–6C)alkenyl, carboxy(3–6C)alkenyl, (5–8C)cycloalkenyl, (3–6C)alkynyl, (2–5C)alkylcarbamoyl, phenylcarbamoyl, benzylcarbamoyl, (1–4C)alkylcarbamoyl (1–4C)alkyl, di(1–4C)alkylcarbamoyl(1–4C)alkyl, (1–4C)haloalkylcarbamoyl(1–4C)alkyl, (1–3C)haloalkyl, (2–6C)hydroxyalkyl, (1–4C)alkoxy(2–4C)alkyl, (1–4C)alkylthio (2–4C)alkyl, (1–4C)alkanesulphinyl(1–4C)alkyl, (1–4C)alkanesulphonyl(1–4C)alkyl, (2–6C)aminoalkyl, (1–4C)alkylamino(1–6C)alkyl, (2–8C)dialkylamino(2–6C)alkyl, (1–5C)cyanoalkyl, 3-amino-3-carboxypropyl, 2-(amidinothio)ethyl, 2-(N-aminoamidinothio)ethyl, tetrahydropyran-2-yl, thietan-3-yl, 2-oxopyrrolidinyl, or 2-oxotetrahydrofuranyl, or $R^8$ is of the formula V:

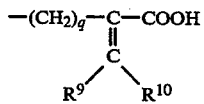

wherein q is one or two and $R^9$ and $R^{10}$ are independently hydrogen or $C_{1-4}$alkyl; or $R^8$ is of the formula VI:

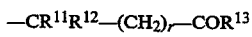

wherein r is 0–3, $R^{11}$ is hydrogen, (1–3C)alkyl or methylthio, $R^{12}$ is hydrogen (1–3C)alkyl, (3–7C)cycloalkyl, cyano, carboxy, (2–5C)carboxyalkyl or methanesulphonylamino, or $R^{11}$ and $R^{12}$ are joined to form, together with the carbon to which they are attached, a (3–7C)carbocyclic ring, and $R^{13}$ is hydroxy, amino, (1–4C)alkoxy, (1–4C) alkylamino or of the formula $NHOR^{14}$ in which $R^{14}$ is hydrogen or (1–4C)alkyl;
or $R^7$ may be of the formula $=CH.R^{15}$ wherein $R^{15}$ is hydrogen, halogen, (1–6C)alkyl, (3–7C)cycloalkyl, (2–6C)alkenyl, (3–7C)cycloalkenyl, phenyl or benzyl;
wherein Q is:
a benzene ring (optionally fused to a further benzene ring so forming a naphthyl group or optionally fused to a 5 or 6 membered heterocyclic aromatic group containing 1, 2 or 3 heteroatoms selected from the nitrogen, oxygen and sulphur), said benzene ring being substituted by groups $R^1$ and $R^2$ which are ortho with respect to one another, wherein $R^1$ is hydroxy or a $C_{1-4}$ alkanoyloxy and $R^2$ is hydroxy, or a $C_{1-4}$ alkanoyloxy,
wherein ring Q (or, in the case wherein ring Q is a benzene ring fused to another benzene ring, either benzene ring) is optionally substituted by $C_{1-4}$ alkyl, halo, hydroxy, hydroxy $C_{1-4}$ alkyl, cyano, trifluoromethyl, nitro, amino, $C_{1-4}$ alkylamino, di-$C_{1-4}$ alkylamino, amino $C_{1-4}$ alkyl, $C_{1-4}$alkylamino $C_{1-4}$ alkyl, di-$C_{1-4}$ alkylamino $C_{1-4}$ alkyl, $C_{1-4}$ alkanoyl, $C_{1-4}$ alkoxy, $C_{1-4}$ alkylthio, $C_{1-4}$ alkanoyloxy, carbamoyl, $C_{1-4}$ alkylcarbamoyl, di-$C_{1-4}$ alkyl carbamoyl, carboxy, carboxy $C_{1-4}$ alkyl, sulpho, sulpho $C_{1-4}$ alkyl, $C_{1-4}$ alkanesulphonamido, $C_{1-4}$ alkoxycarbonyl, $C_{1-4}$ alkanoylamino, nitroso, thioureido, amidino, ammonium, mono-, di- or tri- $C_{1-4}$ alkylammonium or pyridinium, or a 5-membered heterocyclic ring containing 1 to 4 heteroatoms selected from oxygen, nitrogen and sulphur which is optionally substituted by 1, 2 or 3 $C_{1-4}$ alkyl or $C_{1-4}$ alkoxy groups;
Y, which links into the benzene ring, is a covalent bond.

2. The compound according to claim 1 that is 3-(3,4-dihydroxybenzyl)-7-[2-(2-aminothiazol-4-yl)-2-(Z)-1-carboxy-1-methylethoxyimino) acetamido]ceph-3-em-4-carboxylic acid.

3. A pharmaceutical composition that comprises a compound according to claim 1 and a pharmaceutically acceptable carrier.

4. A method of treating a bacterial infection comprising administering to a mammal in need of such treatment an antibacterial effective amount of the compound of claim 1.

* * * * *